US009435724B2

(12) United States Patent
Sanui et al.

(10) Patent No.: US 9,435,724 B2
(45) Date of Patent: Sep. 6, 2016

(54) TEST METHOD AND FIXTURE FOR OBTAINING MATERIAL PROPERTIES UNDER BIAXIAL LOADING

(71) Applicant: The Boeing Company, Chicago, IL (US)

(72) Inventors: Russel J. Sanui, Fountain Valley, CA (US); William P. Keith, Lakewood, CA (US); Michael L. Hand, Huntington Beach, CA (US)

(73) Assignee: The Boeing Company, Chicago, IL (US)

( * ) Notice: Subject to any disclaimer, the term of this patent is extended or adjusted under 35 U.S.C. 154(b) by 150 days.

(21) Appl. No.: 14/306,666

(22) Filed: Jun. 17, 2014

(65) Prior Publication Data

US 2015/0362415 A1 Dec. 17, 2015

(51) Int. Cl.
*G01N 3/08* (2006.01)

(52) U.S. Cl.
CPC ......... *G01N 3/08* (2013.01); *G01N 2203/0019* (2013.01); *G01N 2203/0057* (2013.01); *G01N 2203/0067* (2013.01); *G01N 2203/0274* (2013.01); *G01N 2203/0282* (2013.01); *G01N 2203/0658* (2013.01)

(58) Field of Classification Search
CPC .......... G01N 3/08; G01N 2203/0019; G01N 2203/0085; G01N 2203/0254
USPC .................................................. 73/818, 821
See application file for complete search history.

(56) References Cited

U.S. PATENT DOCUMENTS

| | | | | |
|---|---|---|---|---|
| 3,693,424 A * | 9/1972 | Wagle | ...................... | G01N 3/08 73/114.78 |
| 3,797,303 A | 3/1974 | Bascoul et al. | | |
| 4,715,212 A * | 12/1987 | Johanson | .................. | G01N 3/08 73/38 |
| 5,448,918 A | 9/1995 | Tucchio | | |
| 7,536,921 B1 * | 5/2009 | Chu | .......................... | G01N 3/10 73/760 |
| 8,065,929 B2 * | 11/2011 | Yakimoski | ............... | G01N 3/08 73/865.6 |
| 8,365,588 B2 * | 2/2013 | Miyamoto | .......... | G01M 13/005 33/605 |
| 8,950,268 B2 * | 2/2015 | Ota | .......................... | G01N 3/12 73/788 |
| 2009/0084189 A1 * | 4/2009 | McMechan | ............... | G01N 3/12 73/803 |
| 2013/0199304 A1 * | 8/2013 | Hanswillemenke | ..... | G01N 3/02 73/818 |
| 2013/0213120 A1 * | 8/2013 | Lebedev | ................... | G01N 3/32 73/37 |

* cited by examiner

*Primary Examiner* — Freddie Kirkland, III
(74) *Attorney, Agent, or Firm* — Ostrager Chong Flaherty & Broitman P.C.

(57) ABSTRACT

A test method and corresponding fixture design are provided which enable loading a circular test coupon (made, e.g., of ceramic matrix composite material) to failure under biaxial loading conditions while recording strain and temperature. Biaxial loading requires approximately equal loads to be applied in two directions concurrently. The disclosed method uses liquid coolant (e.g., liquid nitrogen) to cool a ring made of metal alloy (e.g., aluminum alloy) that is disposed radially outward from and surrounds the outer edge of the test coupon. The cooled metal alloy ring contracts and compresses the test coupon until failure occurs.

19 Claims, 6 Drawing Sheets

TEST METHOD AND FIXTURE FOR OBTAINING MATERIAL PROPERTIES UNDER BIAXIAL LOADING

BACKGROUND

This disclosure generally relates to process and apparatus for testing composite material. More specifically, the invention relates to processes and apparatus for obtaining properties of composite material under biaxial loading.

Oxide/oxide ceramic matrix composites (CMC) are being considered for use in commercial aircraft engine exhaust washed structures. Biaxial loading is inherent in acoustic, jet engine, exhaust structures when sandwich geometries are employed. There is a need for a test method and fixture design to characterize CMC materials under biaxial loading. There are likely other materials and applications (e.g., polymer composites and pressure vessels) that could be cost effectively characterized with such a test method.

Biaxial testing has been historically difficult to perform successfully. One, current test method for biaxial testing involves a cruciform coupon loaded simultaneously by two perpendicular load cells. This method requires expensive test machines and test coupons, yields unreliable results, and is not applicable to ceramic matrix composites. This method is conducted on polymeric matrix composite coupons with mixed success. Typically ceramic matrix composites fail prematurely in the grips or at the cruciform intersection, resulting in invalid data.

Another method is to load a cylindrical tube axially while pressurizing the interior. This is a complicated and expensive method with limited applicability. For instance, each test article might need to be a 10-inch-long, 10-inch-diameter cylinder, which would be complicated and expensive to make.

A test method is needed to obtain the open hole compression strength for CMC laminates under biaxial loading conditions to enable use of representative strength and failure criteria on applicable CMC structures.

SUMMARY

The subject matter disclosed herein is directed to a test method and corresponding fixture design which enable loading a test coupon (made, e.g., of CMC material) to failure under biaxial loading conditions while recording strain and temperature. Biaxial loading requires approximately equal loads to be applied in two directions concurrently. No external mechanical loading is used. The method uses liquid coolant (e.g., liquid nitrogen) to cool a metal alloy (e.g., aluminum) ring. The cooled metal alloy ring contracts and compresses a test coupon in the form of a circular test coupon until failure occurs. The test coupon, which has a hole in the center, is expected to have a compressive failure initiating at the edge of the center hole with the development of radial cracking.

In accordance with one embodiment, the test assembly comprises an aluminum alloy coolant ring with two or more inlet and outlet ports and one or more channels for liquid nitrogen. This coolant ring is designed to be quickly cooled by liquid nitrogen, yet be sufficiently massive that it can apply high pressures to the test coupon. A test coupon is mounted to the inside of the coolant ring using two aluminum alloy centering rings, ensuring proper location and providing support at the edges. Two metallic stabilization disks (hereinafter "heat sink disks") are attached above and below the coupon in the interior of the test assembly. These disks provide a heat sink for the test coupon to keep the coupon warm and provide support for the coupon to prevent unwanted buckling failures. Once the test apparatus is fully assembled, tests can be conducted with only a supply of liquid nitrogen and standard lab data acquisition system to record strains and temperatures.

The test apparatus and method disclosed in detail below evenly distributes compressive loading around the entire circumference of a CMC laminate disk by cooling the aluminum alloy coolant ring, which then contracts to apply pressure on the outer edge of the coupon until failure of the coupon ensues. This method is relatively inexpensive, has been shown to be successful in testing CMC materials of varying thickness, and can be adapted to determine the strength when damage or holes are present. Tests can be conducted at ambient temperatures. In the alternative, the apparatus could be placed in a thermal chamber and tests could be conducted at other temperatures.

One aspect of the subject matter disclosed in detail below is a method for loading a test coupon, comprising: (a) placing a coolant ring made of metal alloy radially outward from and surrounding an outer circumferential portion of the test coupon, which coolant ring has a channel; and (b) initiating a flow of liquid coolant through the channel that has a temperature less than the temperature of the coolant ring, wherein the inner diameter of the coolant ring and the outer diameter of the test coupon are selected so that the coolant ring will exert radially inwardly directed compressive forces on the outer circumferential portion of the test coupon as the coolant ring is cooled by the liquid coolant. In one implementation, the metal alloy is an aluminum alloy, the test coupon is made of ceramic matrix composite material, and the liquid coolant is liquid nitrogen. The method may further comprise restraining the outer circumferential portion of the test coupon from bending relative to an inner circumferential portion of the test coupon and thermally coupling the inner circumferential portion of the test coupon to a heat sink before cooling.

Another aspect is a test assembly comprising: a test coupon having a hole in the center and an outer circumference, the test coupon comprising an inner circumferential portion adjacent the hole and an outer circumferential portion adjacent the outer circumference; first and second reinforcing rings respectively bonded to respective surfaces of the outer circumferential portion of the test coupon; a coolant ring made of metal alloy disposed radially outward from and surrounding the outer circumferential portion of the test coupon, the coolant ring comprising a first channel; and first and second centering rings coupled to the coolant ring, the first centering ring comprising a first annular projection in contact with the first reinforcing ring, and the second centering ring comprising a second annular projection in contact with the second reinforcing ring. The test assembly may further comprise first and second heat sink disks which are thermally coupled to respective surfaces of the inner circumferential portion of the test coupon. In one implementation, the test coupon has a hole in a center thereof, and the test assembly further comprises: a stud that passes through the hole; and a plurality of nuts that are coupled to the stud, wherein the first and second heat sink disks are coupled to the studs by the nuts.

In accordance with one variation, the coolant ring may have multiple inlets and outlets for the liquid coolant to evenly distribute cooling around the coolant ring. In accordance with another variation, the coolant ring further comprises a first inlet and a first outlet in fluid communication with the first channel, a second channel, and a second inlet and a second outlet in fluid communication with the second channel for enabling counterflowing liquid nitrogen, again to provide more even cooling around the periphery of the coolant channel.

A further aspect is a test coupon assembly comprising: a test coupon having a hole in the center and an outer circumference, the test coupon comprising an inner circumferential portion adjacent the hole and an outer circumferential portion adjacent the outer circumference; and first and second reinforcing rings respectively bonded to opposite surfaces of the outer circumferential portion of the test coupon. In one implementation, the test coupon is made of ceramic matrix composite material and the first and second reinforcing rings are made of graphite/epoxy composite material. The test coupon assembly may further comprise respective pluralities of strain gauges and thermocouples attached to the test coupon.

Yet another aspect is a test system comprising: a coolant ring made of metal alloy and comprising a central opening and a channel surrounding the central opening; first and second centering rings coupled to the coolant ring, the first centering ring comprising a first annular projection which projects into the central opening of the coolant ring, and the second centering ring comprising a second annular projection which projects into the central opening of the coolant ring, the first and second annular projections being separated by a gap; a test coupon disposed in the gap and held by the first and second annular projections; a valve in fluid communication with the channel of the coolant ring; and a source of liquid coolant in fluid communication with the valve. In accordance with one embodiment, the test coupon comprises: a test coupon having a hole in the center and an outer circumference, the test coupon comprising an inner circumferential portion adjacent the hole and an outer circumferential portion adjacent the outer circumference; and first and second reinforcing rings respectively bonded to opposite surfaces of the outer circumferential portion of the circular test coupon. The test system may further comprise first and second heat sink disks which are thermally coupled to respective surfaces of the inner circumferential portion of the test coupon.

Other aspects of test methods and apparatus for biaxially loading a circular test coupon to failure are disclosed and claimed below.

BRIEF DESCRIPTION OF THE DRAWINGS

Reference will hereinafter be made to the drawings in which similar elements in different drawings bear the same reference numerals.

DETAILED DESCRIPTION

The following detailed description is illustrative in nature and not intended to limit claim coverage to the disclosed embodiments or the disclosed applications and uses of the disclosed embodiments.

Figure 1:
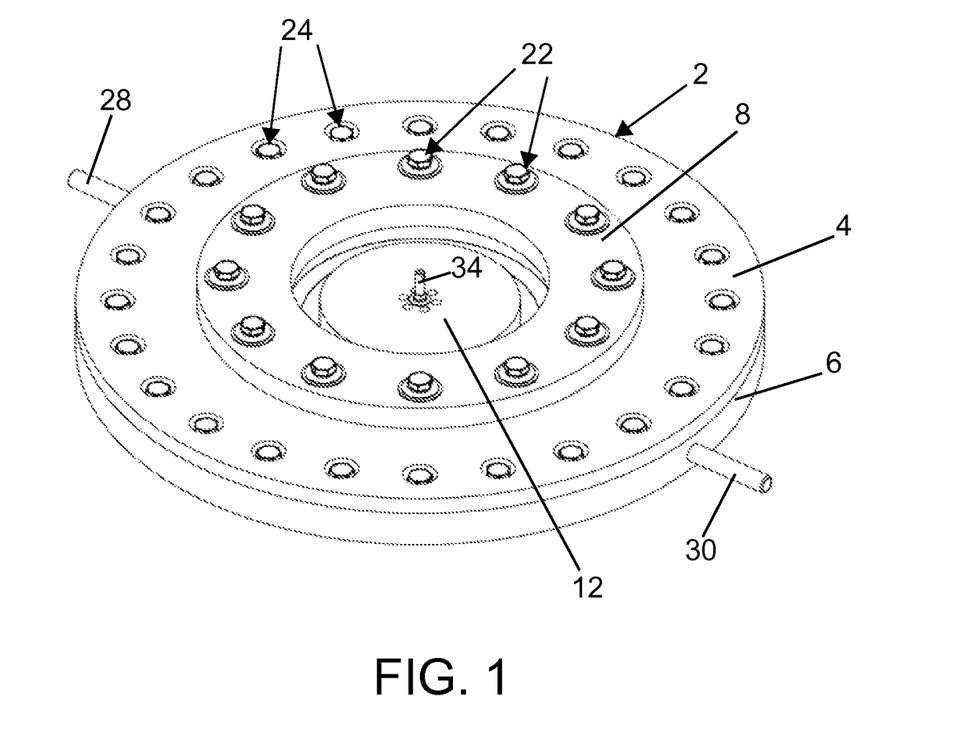
FIG. 1 is a diagram representing an oblique view of a test assembly for biaxially loading a circular test coupon in accordance with one embodiment.
Figure 2:
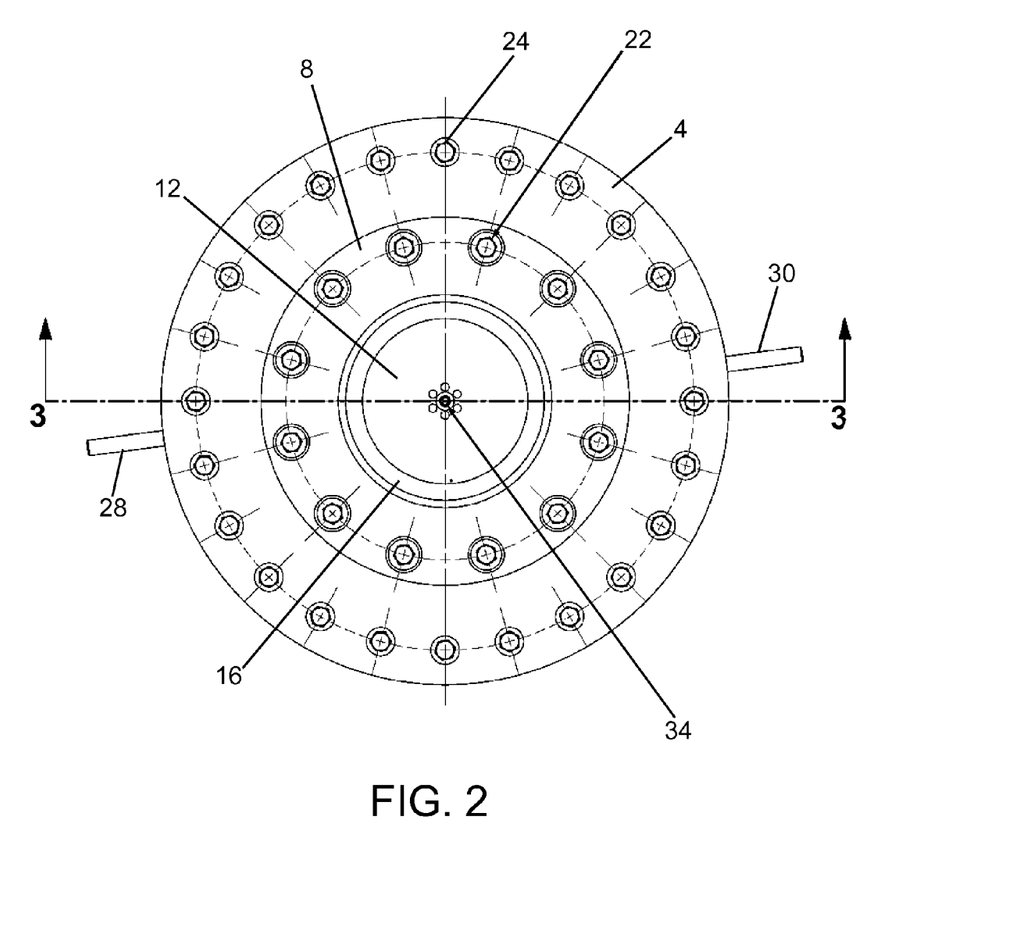
FIG. 2 is a diagram representing a top view of the test assembly depicted in FIG. 1.

FIGS. 1 and 2 are oblique and top views respectively of a test assembly for biaxially loading a test coupon in accordance with one embodiment. A test coupon assembly comprising a circular test coupon 16 (only partially visible in FIG. 2) is held in a test fixture comprising a coolant ring 2, an upper centering ring 8, and a lower centering ring (not visible in FIGS. 1 and 2, but see lower centering ring 10 in FIG. 3). The centering rings are attached to the coolant ring 2 by means of a multiplicity of fastener assemblies 22. The coolant ring 2 is an assembly comprising a top 4 fastened to a base 6 by means of a multiplicity of fastener assemblies 24.

Figure 3:
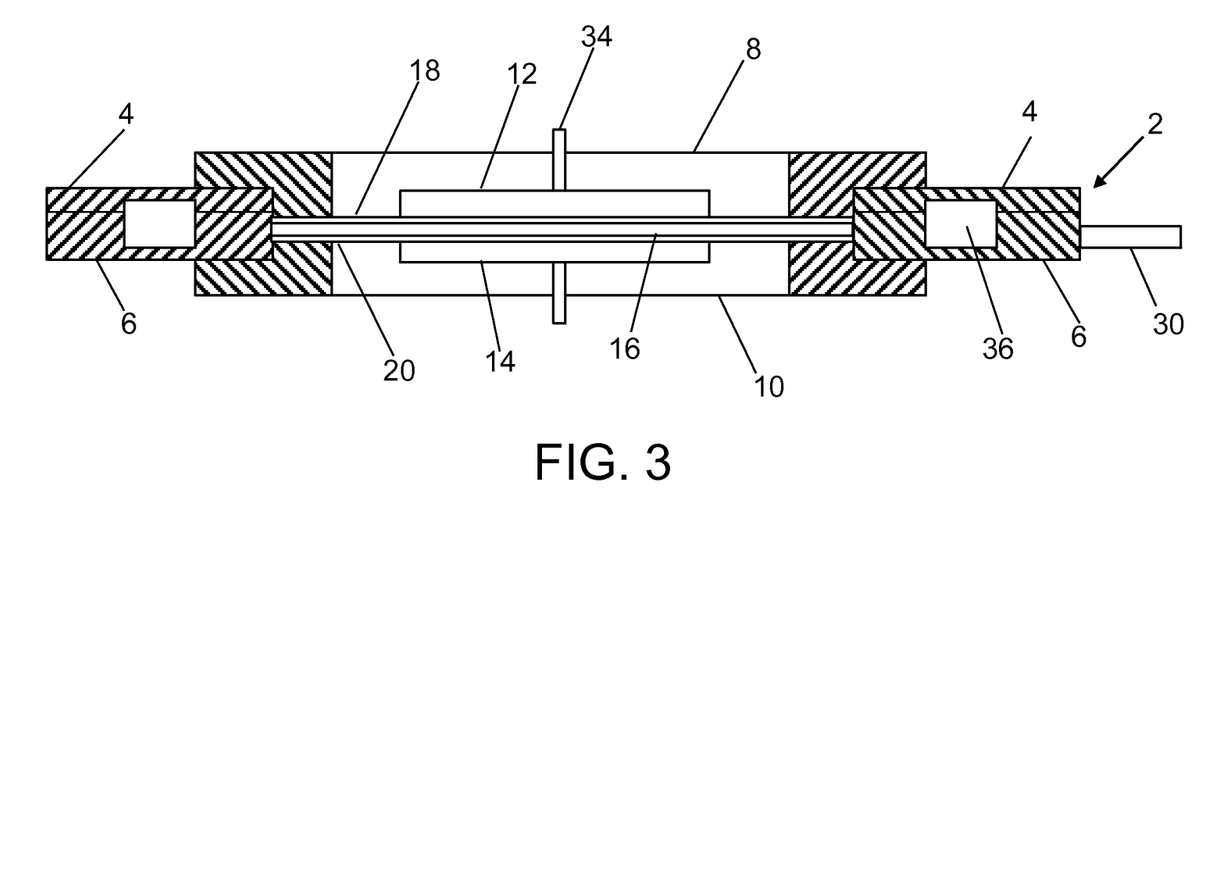
FIG. 3 is a diagram representing a partial sectional view of the test assembly depicted in FIG. 1, the partial section through the coolant ring and the support ring (indicated by hatching) being taken along line 3-3 indicated in FIG. 2.

FIG. 3 is a diagram representing a partial sectional view of the test assembly depicted in FIG. 1, the partial section through the coolant ring 2 and the support rings 8 and 10 being taken along line 3-3 indicated in FIG. 2. As seen in FIG. 3, a circular test coupon 16 is held in a test fixture comprising coolant ring 2, upper centering ring 8, and lower centering ring 10.

The test coupon assembly comprises the test coupon 16 and a pair of first and second reinforcing rings 18 and 20 adhered to the upper and lower surfaces of the outer circumferential portion of the test coupon 16. The reinforcing rings 18 and 20 may, for example, be adhered to the upper and lower surfaces of the test coupon 16 by bonding the reinforcing rings 18 and 20 to the test coupon 16. As seen in FIG. 3, the coolant ring 2 is disposed radially outward from and surrounds the outer circumferential portion of the test coupon 16. The inner radius 44 of coolant ring 2 is preferably equal to or slightly greater than the outer radius of the test coupon 16.

The assembled coolant ring 2 has a coolant channel 36 formed by respective grooves machined into top 4 and base 6 of the coolant ring 2. The coolant channel 36 is in fluid communication with a source (not shown in FIG. 3) of liquid nitrogen (or other suitable liquid coolant). A pair of seal rings (not shown in FIG. 3) are provided at the interface of top 4 and base 6 of the coolant ring 2 to prevent leakage of liquid nitrogen from the coolant channel 36, which is disposed between the inner and outer seal rings. The flow of liquid nitrogen through the coolant channel 36 will cause the coolant ring 2 to contract and exert compressive force on the outer circumference of the test coupon 16 until failure occurs.

The test assembly may further comprise upper and lower heat sink disks 12 and 14, which are thermally coupled to the upper and lower surfaces of an inner circumferential portion of the test coupon 16. In the partial sectional view of FIG. 3, the coolant ring 2 and support rings 8 and 10 are sectioned (indicated by hatching) to reveal the heat sink disks 12 and 14, test coupon 16, and reinforcing rings 18 and 20 (which are not hatched).

Figure 4:
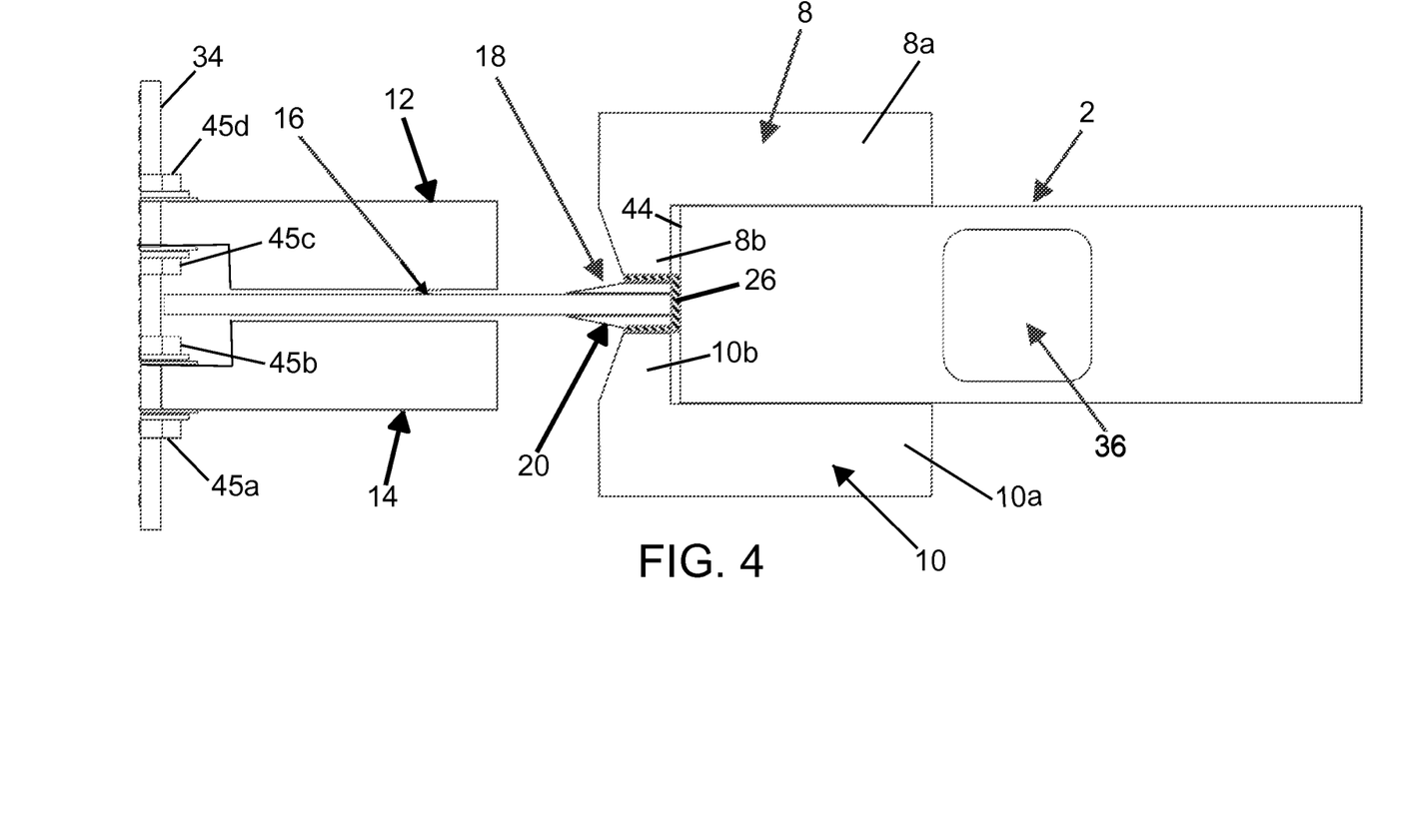
FIG. 4 is a diagram representing a sectional view (without hatching) of a portion of the test assembly depicted in FIG. 1.

As best seen in FIG. 4, the upper heat sink disk 12 is disposed slightly above the test coupon 16, while the lower sink disk 14 is disposed slightly below the test coupon 16, with respective gaps therebetween. The test coupon 16 is thermally coupled to the heat sink disks 12 and 14 by thermal grease (not shown in FIG. 3) that fills the gaps therebetween. The upper sink disk 12 is exposed to the ambient atmosphere by way of a central opening in the upper centering ring 8; the lower sink disk 14 is exposed to the ambient atmosphere by way of a central opening in the lower centering ring 10. While the coolant ring 2 is being cooled, the heat sink disks 12 and 14 keep the test coupon 16 warm and provide support for the test coupon 16 to prevent unwanted buckling failures.

As seen in FIG. 4, the centering rings 8 and 10 comprise respective flanges 8a and 10a integrally formed with and intersecting respective annular projections 8b and 10b. The first centering ring 8 comprises a first annular projection 8b in contact with the first reinforcing ring 18, and the second centering ring 10 comprises a second annular projection 10b in contact with the second reinforcing ring 20. The annular projections 8b and 10b hold the test coupon assembly in a central vertical position relative to the height of the inner radius 44 of the coolant ring 2, which forms a central opening in the coolant ring 2. The annular projections 8b and 10b project into that central opening and hold the test coupon assembly in the gap between the end faces of the annular projections 8b and 10b. Thus the centering rings 8 and 10 restrain the outer circumferential portion of the test coupon 16 from bending or buckling.

Referring still to FIG. 4, when installing the test coupon assembly, the gap between the outer circumferential edge of the test coupon 16 and the inner radius 44 of the coolant ring is filled with a potting compound 26 (e.g., epoxy). The gaps between the annular projections 8b and 10b and the outer circumferential portion of the test coupon 16 are filled with the same potting compound 26.

In the implementation shown in FIG. 4, the test coupon 16 has a hole (see center hole 38 in FIG. 5A) in a center thereof, through which a stud 34 passes. The stud couples the heat sink disks 12 and 14 to each other. The vertical position of the lower heat sink disk 14 relative to stud 34 is fixed by means of nuts 45a and 45b, which threadably engage a lower portion of a threaded shaft of the stud 34. Similarly, the vertical position of the upper heat sink disk 12 relative to stud 34 is fixed by means of nuts 45c and 45d, which threadably engage an upper portion of the threaded shaft of stud 34. The stud 34 does not contact the test coupon 16. Thus the test fixture effectively supports the heat sink disks 12 and 14 by way of the test coupon 16, not by way of the stud 34.

The coolant channel 36 is in fluid communication with inlet fitting 28 and outlet fitting 30, shown in FIGS. 1 and 2. The inlet fitting 28 is connected to a valve (not shown in FIGS. 1 and 2, but see valve 52 indicated in FIG. 7), which is in turn in fluid communication with a source of liquid nitrogen (see liquid nitrogen supply 54 indicated in FIG. 7). When valve 52 is opened, liquid nitrogen will flow through the coolant channel 36, resulting in biaxial compression of the test coupon 16.

In accordance with the implementation depicted in FIGS. 1-4, each of the coolant ring 2, the upper and lower centering rings 8, 10, and the upper and lower heat sink disks 12 and 14 are machined from aluminum alloy plate. The inlet and outlet fittings 28, 30 may comprise aluminum alloy tubing. The preferred aluminum alloy type includes precipitation-hardened aluminum alloys containing magnesium and silicon as their major alloying elements.

Figure 5A:
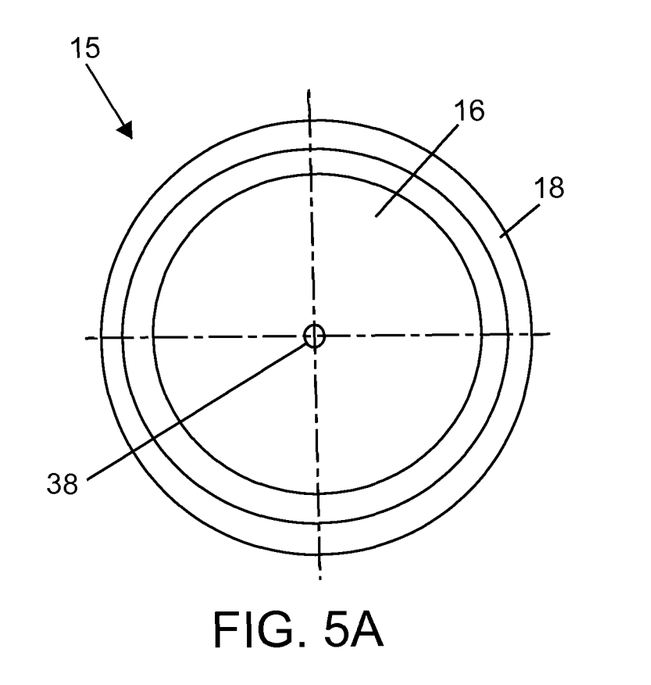
FIGS. 5A and 5B are diagrams representing top and side views respectively of a biaxial test coupon assembly incorporated in the test assembly depicted in FIG. 1.
Figure 5B:
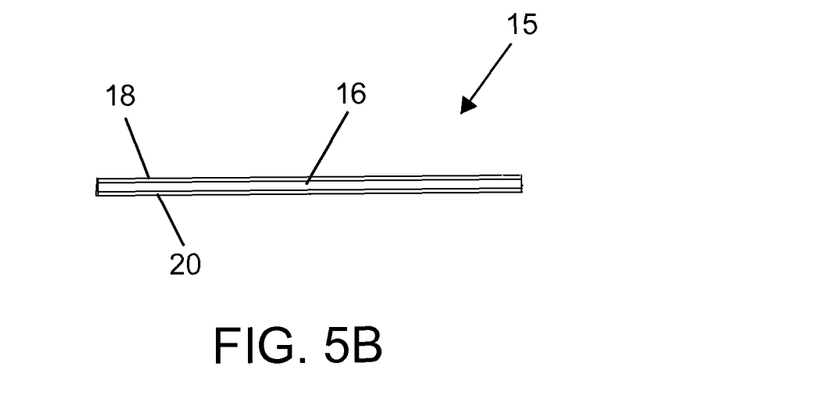

FIGS. 5A and 5B are diagrams representing top and side views respectively of a biaxial test coupon assembly 15 incorporated in the test assembly depicted in FIG. 1. The test coupon assembly 15 comprises a circular test coupon 16 (in the form of a disk) having a hole 38 in the center and an outer circumference. The test coupon 16 comprises an inner circumferential portion adjacent the hole 38 and an outer circumferential portion adjacent the outer circumference. The test coupon assembly 15 further comprises circular reinforcing rings 18 and 20 respectively bonded to opposite surfaces of the outer circumferential portion of the test coupon using film adhesive. The outer circumference of the test coupon assembly 15 is trimmed to a final dimension after bonding. In one implementation, the test coupon 16 is made of ceramic matrix composite material and the reinforcing rings 18 and 20 are made of graphite/epoxy composite material. The test coupon assembly 15 further comprises respective pluralities of strain gauges and thermocouples (not shown in FIG. 5A) attached to the test coupon 16 at specified locations.

Figure 6:
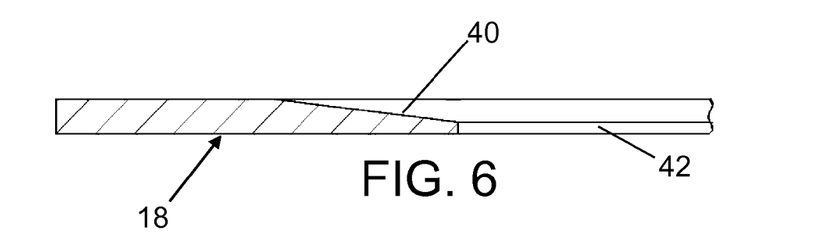
FIG. 6 is a diagram representing a sectional view of a portion of a reinforcement ring incorporated in the test coupon assembly depicted in FIGS. 5A and 5B.

FIG. 6 is a diagram representing a sectional view of a portion of reinforcement ring 18 incorporated in the test coupon assembly depicted in FIGS. 5A and 5B. In this implementation, the reinforcement ring 18 is an annular ring made of graphite/epoxy composite material. Reinforcement ring 18 has a central opening 42 and a beveled surface 40 adjacent the central opening 42. The outer circumferential portion of reinforcement ring 18 is flat. The other reinforcement ring 20 has similar geometry.

Biaxial compression testing can be conducted using a test assembly of the type described above. Liquid nitrogen cooling the room-temperature fixture was the driving force to induce stress in the test coupon. No external mechanical loading was used. Laminate CMC test coupons are expected to experience compressive failure initiating at the edge of the center hole with the development of radial cracking. As the coolant ring and centering rings cool, they contract and apply a compression load to the outer edge of the test coupon and reinforcement rings. At the center hole of the test coupon, there was a stress concentration due to the hole.

The procedure for assembling the test apparatus will now be described with occasional reference to the drawings.

Assemble the Test Coupon Assembly

In accordance with one embodiment, a circular test coupon can be cut from a multi-ply panel made of a CMC composite material. Then a test coupon assembly is created from the circular test coupon of CMC laminate and a pair of graphite/epoxy reinforcement rings. The CMC test coupon and reinforcement rings are individually cut into a rough shape with a specified diameter. A respective reinforcement ring is bonded onto each side of the CMC test coupon using a suitable adhesive cured under full vacuum. Final trimming is performed on the assembly to obtain a specified diameter. Tight circular tolerances are preferred in order to obtain even circumferential loading on the test coupon from the thermally contracting aluminum test fixture. A hole is drilled in the center of each CMC test coupon. Then strain gages and thermocouples are installed on the CMC test coupon at selected positions.

Mount Heat Sinks onto Coupon Assembly

After the test coupon has been assembled, a pair of heat sink disks are mounted on the coupon assembly using a stud 34 and four nuts 45a-45d threaded onto stud 34, as seen in FIG. 4. The heat sink mounting procedure is as follows: (1) install nut 45a near one end of the stud 34; (2) apply thermal grease on the upper side of heat sink disk 14; (3) assemble the CMC coupon (comprising the CMC test coupon 16 and reinforcing rings 18 and 20) and heat sink disk 14 onto the stud 34 with washers and with the thermal grease therebetween; (4) install nut 45b with washer and tighten until snug; (5) install nut 45c with washer and adjust its height; (6) apply thermal grease on the lower surface of heat sink disk 12; (7) install the heat sink disk 12 on nut 45c; and (8) install nut 45d with washer and tighten until snug. The result (seen in FIGS. 3 and 4) is a heat sink/coupon assembly in which both sides of the CMC test coupon 16 are thermally coupled to respective heat sink disks 12 and 14 by means of thermal grease that fills the gaps between the test coupon and the heat sink disks.

Assemble the Coolant Ring

The test fixture is assembled by placing seal rings in respective annular grooves formed in the coolant ring base 6, placing the coolant ring top 4 on top of the coolant ring base 6, and then fastening the top and base together using a multiplicity of fastener assemblies 24. Coolant ring top 4 and coolant ring base 6 have respective machined channels which form the coolant channel 36 when the top and base are fastened together. The seal rings prevent leakage of liquid nitrogen from the coolant channel 36.

Mount Heat Sink/Coupon Assembly in Test Fixture

The final assembly of the test fixture is begun by placing the lower centering ring 10 on blocks above the work surface so that some bolts can be inserted from below. The coolant ring 2 is then located on top of the lower centering ring 10. A thin coat of adhesive 26 is then applied to the face of annular projection 10b of the lower centering ring 10 and to the inner radius 44 of the coolant ring 2 (see FIG. 4). Preferably the adhesive 26 is an epoxy. The test coupon assembly (with heat sinks) is then installed such that the reinforcing ring 20 confronts the face of annular projection 10b of the lower centering ring 10 with adhesive 26 therebetween and the outer circumference of the test coupon 16 confronts the inner radius 44 of coolant ring 2 with adhesive 26 therebetween. With the test coupon assembly seated inside the coolant ring 2, more adhesive 26 is applied to the upper surface of the reinforcement ring 18 of the test coupon assembly. Then the upper centering ring 8 is placed onto the coolant ring 2 so that the face of annular projection 8b of the upper centering ring 8 confronts the reinforcing ring 18 with adhesive 26 therebetween. The upper and lower centering rings 8, 10 and the coolant ring 2 are then fastened together by assembling and torquing the multiplicity of fastener assemblies 22 (shown in FIG. 1). The adhesive 26 is allowed to cure before the test coupon 16 is subjected to biaxial loading.

Setup and Testing

Prior to start of testing, insulation can be installed around the test assembly to minimize the heat transfer to the test fixture during cooling. The insulation should be fabricated to cover the top, bottom and outside edge of the test fixture. A hole should be left open on each side to expose the heat sinks to room temperature air. The hole should be the size of the inner radius of the centering rings. In addition, the insulated test assembly should be placed on blocks so that both heat sinks are exposed to air flow.

Figure 7:
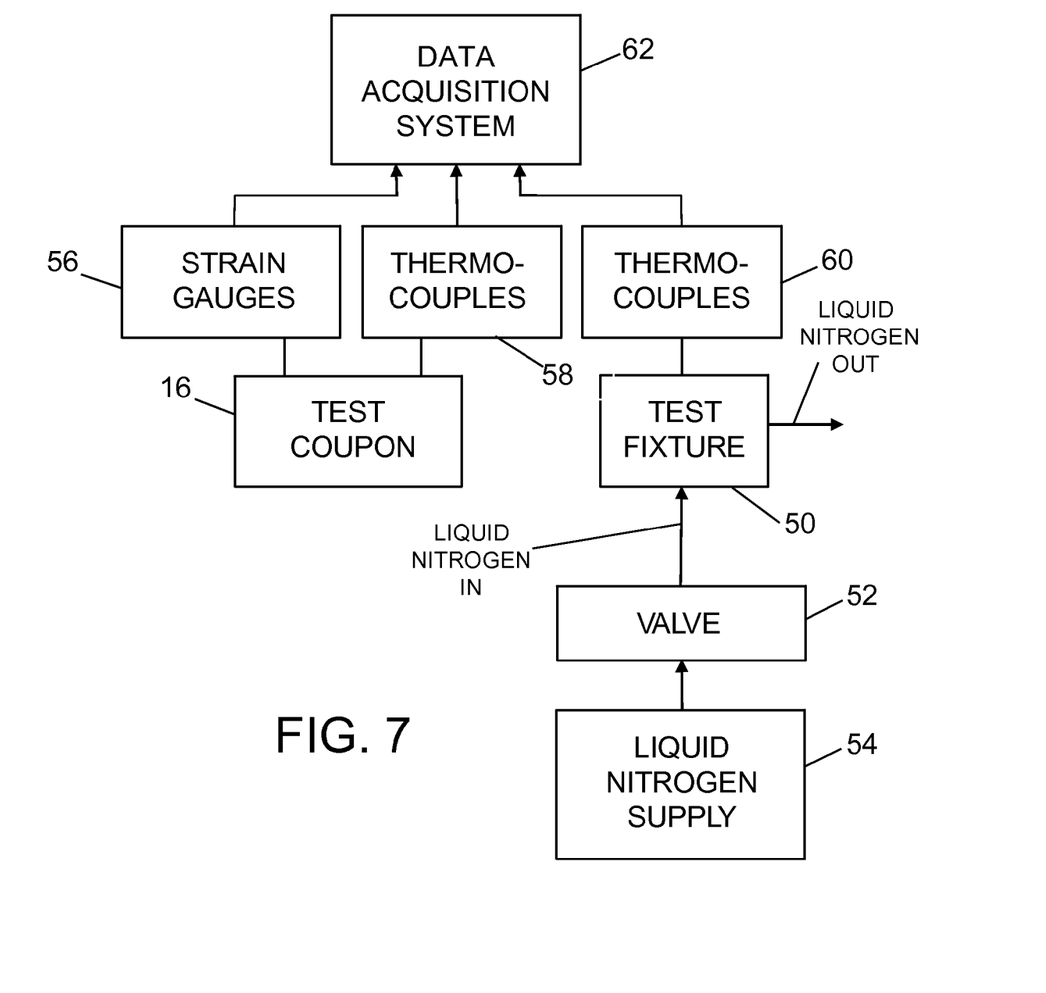
FIG. 7 is a block diagram showing some components of a test system for biaxially loading a circular test coupon in accordance with one embodiment.

Referring to FIG. 7, the liquid nitrogen line is then coupled to the inlet fitting of the test fixture 50 (comprising coolant ring 2 and support rings 8, 10). The liquid nitrogen line from the liquid nitrogen supply 54 (e.g., a cryogenic storage dewar) to the test fixture 50 should be insulated to help keep the nitrogen in liquid form. An outlet hose (not shown in FIG. 7) is attached to the outlet fitting of the test fixture 50.

Upon completion of system set-up, a data acquisition system 62 can be started. In accordance with one possible implementation, data from strain gages 56 and thermocouples 58 attached to the test coupon 16 and from thermocouples 60 attached to the test fixture 50 are captured at a specified rate (e.g., 10 Hz).

Testing is initiated by opening valve 52 to start the flow of liquid nitrogen from the liquid nitrogen supply 54 to the test fixture 50. The technician should monitor the data and listen for signs of failure. An audible cracking sound is usually associated with failure. Strains will drop off after failure. After failure, the flow of liquid nitrogen is stopped.

Minor design adjustments may provide improved performance in certain test situations. In accordance with one variation, more inlet/outlet ports for the liquid nitrogen can be provided in order to even out the temperature distribution. For example, one circular channel may be in fluid communication with two inlets disposed at angular positions of 0 and 180 degrees respectively and two outlets disposed at angular positions of 90 and 270 degrees respectively around the periphery of the coolant channel. A second variation would be to replace the single coolant flow channel in the coolant ring with two side-by-side channels in fluid communication with respective inlets and outlets for enabling counterflowing liquid nitrogen, again to provide more even cooling around the periphery of the coolant channel. In the latter variant, the coolant ring may comprise a grooved top and a grooved base with an annular ring therebetween to close the respective grooves, thereby forming side-by-side channels in the coolant ring. Scaling up the apparatus design to test larger coupons might be one circumstance in which it would be advantageous to use design modifications, such as the two described in this paragraph, to obtain less variation in temperature around the periphery of the test article.

The method disclosed above has the capability to reach the desired stresses in the coupon while using readily available liquid nitrogen and being able to keep the coupon at room temperature so that strain gages can be readily used. Obtaining the strength of the CMC material under biaxial loading enables representative strengths and failure criteria to be applied to CMC structures subjected to biaxial stress and strains.

While apparatus and methods for biaxial loading of a test coupon have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A method for loading a circular test coupon, comprising:
   (a) placing a coolant ring made of metal alloy so that an inner circumferential portion of the coolant ring is disposed radially outward from and surrounding an outer circumferential portion of the test coupon, which coolant ring has a channel; and (b) initiating a flow through the channel of liquid coolant that has a temperature less than the temperature of the coolant ring, wherein the inner diameter of the coolant ring and the outer diameter of the test coupon are selected so that the inner circumferential portion of the coolant ring will exert radially inwardly directed compressive forces on the outer circumferential portion of the test coupon as the coolant ring is cooled by the liquid coolant.

2. The method as recited in claim 1, wherein the metal alloy is an aluminum alloy.

3. The method as recited in claim 1, wherein the test coupon is made of ceramic matrix composite material.

4. The method as recited in claim 1, wherein the test coupon has a hole in a center thereof.

5. The method as recited in claim 1, wherein the liquid coolant is liquid nitrogen.

6. The method as recited in claim 1, further comprising the following step performed prior to step (b): restraining the outer circumferential portion of the test coupon from bending relative to an inner circumferential portion of the test coupon.

7. The method as recited in claim 1, further comprising the following step performed prior to step (a): thermally coupling an inner circumferential portion of the test coupon to a heat sink.

8. A test assembly comprising:
a circular test coupon having a hole in a center and an outer circumference, said test coupon comprising an inner circumferential portion adjacent said hole and an outer circumferential portion adjacent said outer circumference;
first and second reinforcing rings respectively adhered to respective surfaces of said outer circumferential portion of said test coupon;
a coolant ring made of metal alloy and having an inner circumferential portion disposed radially outward from and surrounding said outer circumferential portion of said test coupon, said coolant ring comprising a first channel; and
first and second centering rings coupled to said coolant ring, said first centering ring comprising a first annular projection in contact with said first reinforcing ring, and said second centering ring comprising a second annular projection in contact with said second reinforcing ring.

9. The test assembly as recited in claim 8, wherein said coolant ring has multiple inlets and outlets for the liquid coolant to evenly distribute cooling around said coolant ring.

10. The test assembly as recited in claim 8, wherein said coolant ring further comprises a first inlet and a first outlet in fluid communication with said first channel, a second channel, and a second inlet and a second outlet in fluid communication with said second channel.

11. The test assembly as recited in claim 8, wherein the metal alloy is an aluminum alloy.

12. The test assembly as recited in claim 8, wherein said test coupon is made of ceramic matrix composite material.

13. The test assembly as recited in claim 8, wherein said coolant ring comprises a base and a top coupled to each other by a plurality of fasteners.

14. The test assembly as recited in claim 8, further comprising first and second heat sink disks which are thermally coupled to respective surfaces of said inner circumferential portion of said test coupon.

15. The test assembly as recited in claim 14, wherein the test coupon has a hole in a center thereof, further comprising:
a stud that passes through said hole; and
a plurality of nuts that are coupled to said stud,
wherein said first and second heat sink disks are coupled to said studs by said nuts.

16. A test system comprising:
a coolant ring made of metal alloy and comprising a central opening and a channel surrounding said central opening;
first and second centering rings coupled to said coolant ring, said first centering ring comprising a first annular projection which projects into said central opening of said coolant ring, and said second centering ring comprising a second annular projection which projects into said central opening of said coolant ring, said first and second annular projections being separated by a gap;
a circular test coupon disposed in said gap and held by said first and second annular projections;
a valve in fluid communication with said channel of said coolant ring; and
a source of liquid coolant in fluid communication with said valve.

17. The test system as recited in claim 16, wherein said test coupon has a hole in the center and an outer circumference, said test coupon comprising an inner circumferential portion adjacent said hole and an outer circumferential portion adjacent said outer circumference, and wherein said test system further comprises first and second reinforcing rings respectively bonded to opposite surfaces of said outer circumferential portion of said test coupon.

18. The test system as recited in claim 17, further comprising first and second heat sink disks which are thermally coupled to respective surfaces of said inner circumferential portion of said test coupon.

19. The test system as recited in claim 16, wherein said coolant ring comprises a base and a top coupled to each other by a plurality of fasteners.

* * * * *